US010407667B2

(12) United States Patent
Aubry et al.

(10) Patent No.: US 10,407,667 B2
(45) Date of Patent: Sep. 10, 2019

(54) METHOD FOR RAPID GENERATION OF AN INFECTIOUS RNA VIRUS

(71) Applicants: UNIVERSITÉ D'AIX-MARSEILLE, Marseilles (FR); INSERM (INSTITUT NATIONAL DE LA SANTÉ ET DE LA RECHERCHE MÉDICALE), Paris (FR)

(72) Inventors: Fabien Aubry, Marseilles (FR); Antoine Nougairéde, Marseilles (FR); Gilles Quérat, Cabries (FR); Xavier De Lamballerie, Ensués la Redonne (FR); Ernest Andrew Gould, St Albans (GB); Lauriane De Fabritus, Marseilles (FR)

(73) Assignees: UNIVERSITÉ D'AIX-MARSEILLE, Marseilles (FR); INSERM (INSTITUT NATIONAL DE LA SANTÉ ET DE LA RECHERCHE MÉDICALE), Paris (FR)

( * ) Notice: Subject to any disclaimer, the term of this patent is extended or adjusted under 35 U.S.C. 154(b) by 37 days.

(21) Appl. No.: 15/315,667

(22) PCT Filed: Jun. 19, 2015

(86) PCT No.: PCT/EP2015/063812
§ 371 (c)(1),
(2) Date: Dec. 1, 2016

(87) PCT Pub. No.: WO2015/193472
PCT Pub. Date: Dec. 23, 2015

(65) Prior Publication Data
US 2018/0208907 A1 Jul. 26, 2018

(30) Foreign Application Priority Data
Jun. 20, 2014 (EP) .................................... 14305955

(51) Int. Cl.
*C12N 7/02* (2006.01)
*C12N 7/00* (2006.01)
*A61K 39/00* (2006.01)

(52) U.S. Cl.
CPC ................. *C12N 7/02* (2013.01); *C12N 7/00* (2013.01); *A61K 2039/525* (2013.01); *C12N 2770/24051* (2013.01); *C12N 2770/24151* (2013.01); *C12N 2999/007* (2013.01); *Y02A 50/383* (2018.01); *Y02A 50/386* (2018.01); *Y02A 50/388* (2018.01); *Y02A 50/39* (2018.01); *Y02A 50/394* (2018.01); *Y02A 50/396* (2018.01); *Y02A 50/51* (2018.01)

(58) Field of Classification Search
None
See application file for complete search history.

(56) References Cited

PUBLICATIONS

Siridechadilok B, et al. "A Simplified Positive-Senese-RNA Virus Construction Approach That Enchances Analysis Throughput", Journal of Virology, vol. 87, No. 23, Dec. 1, 2013.

Aubry F., et al. "Single-stranded positive-sense RNA viruses generated in days using infectious subgenomic amplicons" Journal of General Virology, vol. 95, No. Pt 11, Jul. 22, 2014.

Aubry, Fabien et al. "Flavivirus reverse genetic systems, construction techniques and applications:A historical perspective", Antiviral Research, vol. 114, Dec. 12, 2014.

*Primary Examiner* — Stacy B Chen
(74) *Attorney, Agent, or Firm* — McAndrews, Held & Malloy, Ltd.

(57) ABSTRACT

The present invention relates to a method for rapid generation of an infectious RNA virus that completely eliminates the need of constructing a full-length c DNA, which covers the entire viral genome, cloning and propagating such full length c DNA.

17 Claims, 1 Drawing Sheet

Specification includes a Sequence Listing.

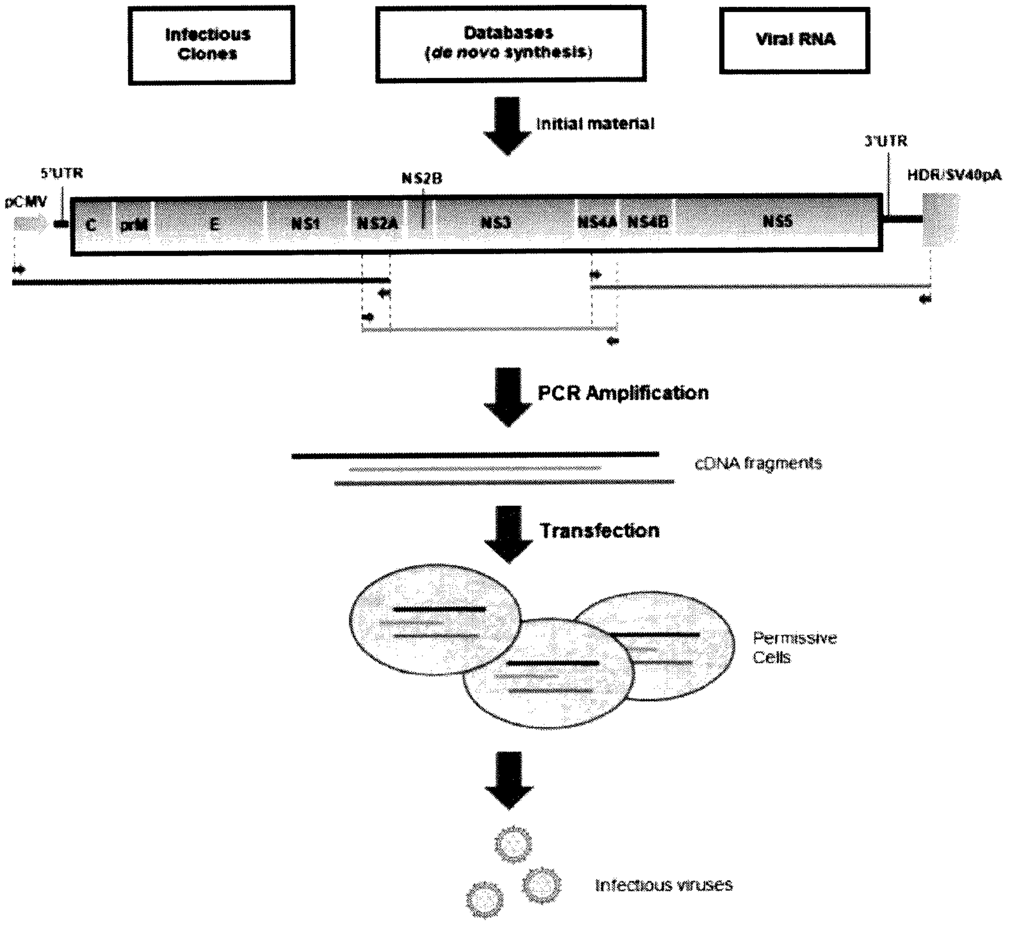
Infectious Clones
Databases (de novo synthesis)
Viral RNA
Initial material
5'UTR
pCMV
C
prM
E
NS1
NS2A
NS2B
NS3
NS4A
NS4B
NS5
3'UTR
HDR/SV40pA
PCR Amplification
cDNA fragments
Transfection
Permissive Cells
Infectious viruses

METHOD FOR RAPID GENERATION OF AN INFECTIOUS RNA VIRUS

The present patent application is filed pursuant to 35 U.S.C. 371 as a U.S. National Phase application of International Patent Application No. PCT/EP2015/063812, which was filed Jun. 19, 2015, claiming the benefit of priority to European Patent Application No. 14305955.8 (EP), which was filed on Jun. 20, 2014. The content of each of the aforementioned patent applications incorporated herein by reference in its entirety.

FIELD OF THE INVENTION

The present invention relates to a method for rapid generation of an infectious RNA virus that completely eliminates the need of constructing a full-length cDNA, cloning and propagating of such full-length cDNA.

BACKGROUND OF THE INVENTION

Development of molecular methods that enable production of infectious virus from DNA copies of their genomes has significantly improved our knowledge of RNA virus life cycles and pathogenesis, by permitting the development of "reverse genetics", i.e., studies of the impact of specific mutations on the biological properties of viruses.

However, current methodologies for construction of infectious cDNA clones are unpredictable and laborious processes frequently associated with undesirable mutations or unstable/toxic clones in bacteria.

This has spawned great interest in alternative methods for generating RNA virus. Various methodological improvements, such as the use of alternative hosts, low-copy-number plasmids, cosmid vectors, bacterial artificial chromosomes, modified promoters or modified viral genome sequences with reduced cryptic bacterial promoter activity have been proposed.

Bacterium-free approaches were also developed for example with Tick-borne encephalitis (TBEV) by Gritsun and Gould in 1995 and with West Nile virus (WNV) and Dengue virus (DENV) by Edmonds et al. and Siridechadilok et al., respectively, in 2013.

Although they represented significant advances, these methods require substantial optimisation for each virus studied and do not provide a unified methodological process.

There is thus a long felt unfulfilled need for an alternative method for generating an infectious RNA virus, which is efficient, precise and prompt.

SUMMARY OF THE INVENTION

The inventors have shown that overlapping cDNA fragments, each covering a portion of the genome of a RNA virus, can give rise to a replicating virus without the use of a full-length cDNA or a plasmid or a vector comprising such full length cDNA.

The inventors thus put light that overlapping double-stranded DNA fragments, each covering a portion of the viral genome, spontaneously enable recombination and synthesis of a DNA copy of the complete viral genome in cellulo.

Consequently, in a first aspect, the invention relates to a method for generating an infectious RNA virus comprising the following steps:

a) introduction of a promoter of DNA-dependent RNA polymerase in position 5' and optionally a terminator and a RNA polyadenylation sequence in position 3' of the entire genome of a RNA virus;

b) amplification of the entire viral genome as prepared in step a) including said promoter and optionally said terminator and RNA polyadenylation sequence, in at least 2, preferably at least 3, 4, 5 or 6 overlapping cDNA fragments;

c) transfection of said cDNA fragments into a host cell;

d) incubation of the host cell of step c); and e) recovery of the infectious RNA virus from said incubated host cell.

In a second aspect, the invention pertains to the use of the method for generating an infectious RNA virus as disclosed herein, and/or of the RNA virus obtained according to said method, for reverse genetic analysis.

In a third aspect, the invention relates to the use of the method for generating an infectious RNA virus as disclosed herein, and/or of the RNA virus obtained according to said method, for the safe and efficient shipment of infectious RNA virus.

DETAILED DESCRIPTION OF THE INVENTION

The inventors founded out that overlapping double-stranded DNA fragments, each covering a portion of the viral genome, spontaneously enable recombination and synthesis of a DNA copy of the complete viral genome after transfection. Based on this surprising discovery, the inventors developed a novel approach for generating an infectious RNA virus which does not require cloning and propagation of a full-length cDNA into bacteria.

In a first aspect, the invention thus relates to a method for generating an infectious RNA virus comprising the following steps:

a) introduction of a promoter of DNA-dependent RNA polymerase in position 5' and optionally a terminator and a RNA polyadenylation sequence in position 3' of the entire genome of a RNA virus;

b) amplification of the entire viral genome as prepared in step a) including said promoter and optionally said terminator and RNA polyadenylation sequence, in at least 2, preferably at least 3, 4, 5 or 6 overlapping cDNA fragments;

c) transfection of said cDNA fragments into a host cell;

d) incubation of the host cell of step c); and e) recovery of the infectious RNA virus from said incubated host cell.

Based on their thorough researches, the inventors overcame a technical prejudice by developing a method which exonerates from:

constructing a full length cDNA, covering the entire viral genome; and/or the use of a plasmid or a vector comprising such full length cDNA; and/or the necessity of reconstructing the full length cDNA or the entire viral genome before transfection into a host cell; and/or modifying the viral genome such as incorporating not naturally occurring recombination or restriction enzyme site; and/or using of helper virus or other viral protein.

The method of the invention, also referred to as "Infectious Subgenomic Amplicons" or "ISA", is thus a very simple procedure able to expedite production of infectious RNA viruses within days, with perfect control of the viral sequences and starting from a variety of initial sources including pre-existing infectious clones, viral RNA or de novo synthesized DNA genomic sequences. Unlike the other bacterium free approaches, disclosed in prior art, the method of the invention does not require any additional step beside preparation of cDNA fragments. The assembly of the construct is not made in vitro by Gibson assembly or circular polymerase extension cloning before the transfection but through a recombination process that directly takes place in cellulo which greatly facilitates and shortens the methodology.

As used herein, the expression "generation of infectious RNA viruses" refers to the production of a RNA virus, in a wild type form or genetically modified form, according to the method of the invention. The term "infectious virus" refers to a virus having the ability to reproduce, i.e. able to amplify the viral genome in a host cell, the packaging of the viral genome in a cell and/or the release of infectious viral particles from a cell. It is noteworthy that a virus can be pathogenic or non pathogenic and still be infectious.

As used herein, the expression "not naturally occurring recombination site" refers to sequences allowing site-specific recombination that can be exemplified by the Cre-Lox or FLP-FRT recombination systems. Restriction enzyme site refers to sequences allowing site-specific cutting of double stranded DNA by restriction enzymes that can be exemplified by the NotI or AluI endonucleases.

Preferably, the infectious RNA virus that the method aims to generate (also referred to as "target virus" herein) is a single stranded positive or negative RNA virus. More preferably, said virus is a single stranded positive RNA virus. More preferably, said virus is selected from the group consisting of flavivirus, alphavirus and enterovirus.

A non-limiting list of flaviviruses comprises Dengue virus (DENV), Yellow fever virus (YFV), St Louis encephalitis (SLEV), Japanese encephalitis viruses (JEV), Murray Valley encephalitis (MVEV), West Nile virus (WNV), Rocio (ROCV), Tick-borne encephalitis virus (TBEV), Omsk hemorrhagic fever (OMSKV), Kyasanr Forrest disease (KFDV), Powassan (POWV). Preferably, said flavivirus is selected from the group consisting of:

- Japanese encephalitis viruses (JEV); such as a genotype I strain (JEV I) or a genotype III strain (JEV III),
- West Nile virus (WNV), such as a genotype 2 strain;
- Dengue virus (DENV), such as a serotype 4 strain;
- Yellow fever virus (YFV), such as a South American wild-type strain; and
- Tick-borne encephalitis virus (TBEV), such as a Far-Eastern subtype strain.

More preferably, said flavivirus is dengue virus.

A non-limiting list of alphaviruses comprises Chikungunya virus (CHIK), Eastern equine encephalitis (EEE), Western equine encephalitis virus, Venezuelan equine encephalitis virus (VEE), Mayaro virus (MAY), O'nyong'nyong virus (ONN), Sindbis virus, Semliki Forest virus, Barmah Forest virus, Ross River virus, Una virus, Tonate virus. Preferably, said alphavirus is Chikungunya virus.

A non-limiting list of enteroviruses comprises Coxsackie, Echovirus, Poliovirus, and Rhinovirus. Preferably, said enterovirus is Coxsackie, more preferably Coxsackie B virus.

Alternatively, said virus is a single-stranded negative strand RNA virus. More preferably, said virus is a paramyxovirus, an arenavirus, a filovirus, a rhabdovirus, a bunyavirus or an influenza virus.

The method of the invention comprises a step a) of introducing a promoter of DNA-dependent RNA polymerase in position 5' of the entire genome of a RNA virus. Optionally, said step a) further comprises the introduction of a terminator and a RNA polyadenylation sequence in position 3' of the entire genome of a RNA virus.

It is noteworthy that when the genome of the target virus is poly-adenylated, such as alphavirus genome, step a) is a step of introducing a promoter of DNA-dependent RNA polymerase in position 5' and a terminator and a RNA polyadenylation sequence in position 3' of the entire genome of a RNA virus.

By including, at the 5' terminus of the first cDNA fragment, a promoter of DNA-dependent RNA polymerase, and at the 3' terminus of the last cDNA fragment a ribozyme sequence and a signal sequence for RNA poly-adenylation, the cDNA fragments are transcribed as a full-length RNA genome with authentic 5' and 3' termini.

Preferably, said promoter of DNA-dependent RNA polymerase in position 5' is the human cytomegalovirus promoter (pCMV), as depicted in SEQ ID No 1. Preferably, said terminator and RNA polyadenylation sequence is respectively the hepatitis delta ribozyme and the simian virus 40 polyadenylation signal (HDR/SV40 pA). The sequence of HDR/SV40 pA is depicted in SEQ ID No: 2.

Consequently, step a) provides for the complete viral genome of the infectious RNA virus to generate, flanked respectively in 5' and 3' by the human cytomegalovirus promoter (pCMV) (SEQ ID No:1) and the hepatitis delta ribozyme followed by the simian virus 40 polyadenylation signal (HDR/SV40 pA) (SEQ ID No:2).

The method of the invention comprises a step b) of amplification of the entire viral genome in several overlapping cDNA fragments.

In step b), the entire viral genome corresponds to the entire viral genome as prepared in step a), i.e. which includes said promoter and optionally said terminator and RNA polyadenylation sequence.

As used herein, the expression "overlapping cDNA fragments", cDNA fragments", also designated as "amplicons" or "DNA subgenomic fragments" or "subgenomic amplicons" are double-stranded DNA fragments covering only a portion of the viral genome of a RNA virus. Such fragments correspond to "subgenomic fragments". The inventors enlightened that, when such fragments are transfected within a cell, they surprisingly spontaneously recombine in cellulo to reconstitute the entire viral genome. Said recombination occurs even if the viral genome is not genetically modified to incorporate additional and not naturally occurring recombination site. Put in other words, said recombination occurs with wild type viral genomes.

cDNA fragments according to the invention encompass:

- DNA fragments obtained by amplification, for example by PCR; as well as
- DNA fragments obtained de novo.

Typically, said cDNA fragments may be infectious or non-infectious.

As used herein, the expression "full-length cDNA", refers to a DNA which comprises the entire viral genome of a virus into a single piece.

As used herein, the expression "cDNA fragment covering a portion of the entire viral genome", refers to a DNA fragment which comprises a portion of the entire viral genome. Typically, the cDNA fragments according to the invention recombine spontaneously upon transfection in cells to constitute a DNA copy of the entire viral genome, flanked at the 5' terminus by a promoter of DNA-dependent RNA polymerase, and at the 3' terminus by a termination sequence and a signal sequence for RNA poly-adenylation.

This construct is transcribed as a full-length RNA genome with authentic 5' and 3' termini by the cellular machinery.

On the contrary, a "full-length cDNA covering the entire viral genome" is a single cDNA which encodes for the totality of the viral genome.

Preferably, step b) of the method of the invention allows the production of from 2 to 15 overlapping cDNA fragments, preferably of 3, 4, 5, or 6 overlapping cDNA fragments. Typically, said cDNA fragments are of about 2 kb to about 6 kb, preferably of about 4 kb and each cDNA fragment has 70 to 100 bp overlapping regions.

Preferably, said overlapping cDNA fragments of step b) are:

- fragments of infectious clone not amplified by PCR;
- fragments of infectious clone amplified by PCR;
- fragments of non infectious clone not amplified by PCR;
- fragments of non infectious clone amplified by PCR;
- fragments synthesised de novo not amplified by PCR;
- fragments synthesised de novo amplified by PCR; and
- fragments obtained by reverse-transcription PCR from the viral genome.

In a preferred embodiment, said overlapping cDNA fragments may be obtained thanks to the primers disclosed in the table as follows, depending on the target virus to generate:

| Virus | cDNA fragment to obtain | Primer Forward to use SEQ ID No: | Primer Reverse to use SEQ ID No: |
|---|---|---|---|
| JEV I | I | 3 | 4 |
| | II | 5 | 6 |
| | III | 7 | 8 |
| JEV II | I | 9 | 10 |
| | II | 11 | 12 |
| | III | 13 | 14 |
| WNV | I | 15 | 16 |
| | II | 17 | 18 |
| | III | 19 | 20 |
| TBEV | I | 21 | 22 |
| | II | 23 | 24 |
| | III | 25 | 26 |
| YFV | I | 27 | 28 |
| | II | 29 | 30 |
| | III | 31 | 32 |
| DENV-4 | I | 33 | 34 |
| | II | 35 | 36 |
| | III | 37 | 38 |
| JEV I 6 fragments | I | 39 | 40 |
| | II | 41 | 42 |
| | III | 43 | 44 |
| | IV | 45 | 46 |
| | V | 47 | 48 |
| | VI | 49 | 50 |
| CHIKV | I | 51 | 52 |
| | II | 53 | 54 |
| | III | 55 | 56 |
| CV-B3 | I | 57 | 58 |
| | II | 59 | 60 |
| | III | 61 | 62 |

Said primers are useful for obtaining overlapping cDNA fragments by PCR.

Consequently, in one embodiment, step b) of the method of the invention is a step of amplification of the entire viral genome as prepared in step a):

- in 3 overlapping cDNA fragments using the primers as depicted in SEQ ID No 3 to SEQ ID No: 8, or in 6 overlapping cDNA fragments using the primers as depicted in SEQ IN No: 39 à 50, when said infectious RNA virus is JEV I; or
- in 3 overlapping cDNA fragments using the primers as depicted in SEQ ID No: 9 to SEQ ID No: 14, when said infectious virus RNA is JEV II; or
- in 3 overlapping cDNA fragments using the primers as depicted in SEQ ID No: 15 to SEQ ID No: 20, when said infectious RNA virus is WNV; or
- in 3 overlapping cDNA fragments using the primers as depicted in SEQ ID No: 21 to SEQ ID No: 26, when said infectious RNA virus is TBEV; or
- in 3 overlapping cDNA fragments using the primers as depicted in SEQ ID No: 27 to SEQ ID No: 32, when said infectious RNA virus is YFV; or
- in 3 overlapping cDNA fragments using the primers as depicted in SEQ ID No: 33 to SEQ ID No: 38, when said infectious RNA virus is DENV-4; or
- in 3 overlapping cDNA fragments using the primers as depicted in SEQ ID No: 51 to SEQ ID No: 56, when said infectious RNA virus is CHIKV; or
- in 3 overlapping cDNA fragments using the primers as depicted in SEQ ID No: 57 to SEQ ID No: 62, when said infectious RNA virus is CV-B3.

The method of the invention comprises a step c) of transfection of said cDNA fragments into a host cell.

As used herein, the term "transfection" refers to the introduction of nucleic acids (either DNA or RNA) into eukaryotic or prokaryotic cells or organisms. A cell that has taken up the exogenous nucleic acid is referred to as a "host cell" or "transfected cell." Transfection may be accomplished by a variety of means known in the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

Preferably, the host cell of step c) is a permissive cell, which enables the recovery of an infectious virus. Typically, permissive cells employed in the method of the present invention are cells which, upon transfection with the cDNA fragments, are capable of realising a complete replication cycle of the virus, including the production of viral particles. Preferably, said host cell is selected from the group consisting of SW13, BHK-21, HEK 293 and Vero cell lines.

In a preferred embodiment, step c) is a step of direct transfection of the cDNA fragments obtained in step b) as such, and step c) occurs directly after step b). In this specific embodiment, cDNA fragments as such are transfected into the host cells. Said fragments spontaneously recombine in cellulo into a DNA copy of the entire viral genome flanked at the 5' terminus by a promoter of DNA-dependent RNA polymerase, and at the 3' terminus by a termination sequence and a signal sequence for RNA poly-adenylation. As previously mentioned, the method of the invention overcomes a technical prejudice since it exonerates from transfecting a full length cDNA, covering the entire viral genome, as such. Besides, the method is free from using a plasmid or a vector comprising said full-length cDNA as such and/or the necessity of reconstructing the full cDNA or the entire viral genome before transfection into a host cell. On the contrary, the method relies on the transfection of the overlapping cDNA fragments, each comprising a portion of the viral genome. The transfection of overlapping double-stranded DNA fragments, covering the entire genome of an RNA virus, into permissive cells enables recombination and synthesis of a DNA copy of the complete viral genome in cellulo.

In an alternative embodiment, step c) is a step of transfection of plasmids each comprising a cDNA fragment obtained in step b), wherein each cDNA fragment is incorporated in individual and separate plasmids or vectors. In this embodiment, each cDNA fragment is incorporated into individual and separate plasmids or vectors. Each plasmid or vector comprises a single fragment of cDNA. In this embodiment, the entire viral genome is reconstituted after transfection.

In one embodiment, the method of the invention comprises a further step b') after step b) and prior to step c) of purification of the overlapping cDNA fragments. Said purification can be performed by any known techniques, preferably through a chromatography column.

The method of the invention comprises a step d) of incubation of the host cells, which preferably lasts from 3 to 9 days. During said incubation step, the transfected cDNA fragments spontaneously recombine in the host cells to constitute a DNA copy of the entire viral genome, flanked at the 5' terminus by a promoter of DNA-dependent RNA polymerase, and at the 3' terminus by a termination sequence and a signal sequence for RNA poly-adenylation. This construct is transcribed as a full-length RNA genome with authentic 5' and 3' termini by the cellular machinery.

In an alternative embodiment, the invention relates to a method for generating an infectious RNA virus in vivo.

In this embodiment, said method comprises the following steps:

a) introduction of a promoter of DNA-dependent RNA polymerase in position 5' and optionally a terminator and a RNA polyadenylation sequence in position 3' of the entire genome of a RNA virus;
b) amplification of the entire viral genome as prepared in step a) including said promoter and optionally said terminator and RNA polyadenylation sequence, in at least 2, preferably at least 3, 4, 5 or 6 overlapping cDNA fragments;
c') inoculation of said cDNA fragments into an animal model;
e') recovery of the infectious RNA virus from a biological sample obtained from said animal.

All the previously disclosed technical data are applicable here.

As used herein, the expression "animal model" is a multicellular heterotrophic eukaryote, preferably a mammal, more preferably a non-human mammal. In a preferred embodiment, said animal model is a rodent, more preferably a mouse.

As used herein, the term "biological sample" as used herein refers to any biological sample obtained from the animal model. In the method of the present invention, the sample may comprise any body fluid. Examples of test samples include blood, serum, plasma, nipple aspirate fluid, urine, saliva. Alternatively, said biological sample is a tissue obtained from said animal model. Preferably, said biological sample is selected from the group consisting of adipose tissue, mesangial tissue, hepatic tissue, pancreatic tissue, muscle tissue, blood-vessel tissue, neural tissue and brain and spleen tissue. More preferably, said biological sample is brain and spleen tissue.

As used herein, the term "individual" refers to an animal, in some embodiments a mammal, and in some embodiments a human.

Typically, the step c') of "inoculation of said cDNA fragments into an animal model refers to a step in which cDNA fragments refers to a step of administration to the animal model. Put in other words, said step preferably allows the introduction of the cDNA fragment within the animal model or cells of said model. The cDNA fragments may be delivered or administered to a subject or cell using a variety of means, including, but not limited to oral, intradermal, ophthalmic, sublingual, buccal, intramuscular, intraveneous, intra-arterially, nasal, intraperitoneal, intracranial, intracerebroventricular, intracerebral, intravaginal, intrauterine, rectal, parenteral. Preferably, step c') is performed by intraperitoneal injection, intradermal injections or intracerebral injection.

In a second aspect, the invention pertains to the use of the method for generating an infectious RNA virus as disclosed herein, and/or of the RNA virus obtained according to said method, for reverse genetic analysis.

The method of the invention has the potential to generate the design of large reverse genetics experiments for RNA viruses. It also has the capacity, specifically to modulate the characteristics of the viruses recovered from experimental procedures. Additionally, because DNA subgenomic fragments can conveniently be obtained by PCR, this method has the potential to conserve the genetic diversity of viral populations when starting from viral RNA. Error-prone PCR may be also be used to create artificial viral heterogeneity, e.g. for facilitating the selection of adapted viruses under various experimental selection conditions and, conversely, high-fidelity polymerases and clonal amplification templates may be used to control the degree of clonality of the viruses produced.

All the previously disclosed technical data are applicable here.

In a third aspect, the invention relates to the use of the method for generating an infectious RNA virus as disclosed herein, and/or of the RNA virus obtained according to said method, for the safe and efficient shipment of infectious RNA virus. Indeed, the method of the invention dramatically improves the safety and security of exchanges of RNA viruses, for example between scientific institutions. Indeed, said exchanges can take the form of separate shipment at room temperature of simple, non-infectious, DNA subgenomic fragments. Said fragments could then be combined and transfected by the recipient institute. The method thus enables rapid, simple and safe recovery of the infectious viral strain.

All the previously disclosed technical data are applicable here.

The following examples are given for the purpose of illustrating various embodiments of the invention and are not meant to limit the present invention in any fashion.

FIGURES LEGENDS

FIG. 1: Universal strategy to rescue infectious single stranded positive RNA viruses The entire viral genome, schematically represented in the figure (flaviviral genome), flanked respectively in 5' and 3' by the human cytomegalovirus promoter (pCMV) and the hepatitis delta ribozyme followed by the simian virus 40 polyadenylation signal (HDR/SV40 pA), was amplified by PCR in 3 overlapping cDNA fragments. Transfection of PCR products into permissive cells enabled the recovery of infectious viruses after 3 to 9 days. Horizontal blue arrows represent primers used to generate the 3 overlapping cDNA fragments.

EXAMPLES

Example 1

ISA Method

Methods

Cells, Viruses, Infectious Clones and Antibodies

Baby hamster kidney (BHK-21) cells were grown at 37° C. with 5% CO2 in a minimal essential medium (Life Technologies) with 7% heat-inactivated foetal bovine serum (FBS; Life Technologies) and 1% Penicillin/Streptomycin (PS; 5000 U/mL and 5000 μg/ml; Life Technologies). Human embryonic kidney 293 (HEK-293) cells and African green monkey kidney (VeroE6) cells were grown at 37° C. with 5% CO2 in the same medium than BHK-21 cells supplemented with 1% of non-essential amino acids (Life technologies). Human adrenal carcinoma (SW13) cells were grown at 37° C. with 5% CO2 in RPMI 1640 medium (Life Technologies) with 10% FBS and 1% PS. JEV genotype I strain JEV_CNS769_Laos_2009 (KC196115) was isolated in June 2009 from the cerebrospinal fluid of a patient in Laos16; YFV strain BOL 88/1999 (KF907504), isolated in 2009 from a human serum, was kindly provided by the National Center of Tropical Diseases (CENETROP), Santa-Cruz, Bolivia; DENV-4 strain Dak HD 34 460 (KF907503), isolated from a human serum, was kindly provided by Robert B Tesh from the Center for Biodefense and Emerging Infectious Diseases-Sealy Center for Vaccine Development (University of Texas Medical Branch, Galveston, Tex., USA); the infectious clone of JEV genotype III derived from the strain rp9 (DQ648597) was kindly provided by Yi-Ling Lin from the Institute of Biomedical Sciences, Academia Sinica, Taipei, Taiwan; the infectious clone of WNV was derived from the strain Ouganda 1937 (M12294); the infectious clone of TBEV was derived from the strain Oshima 5.10 (AB062063); the infectious clone of CV-B3 was derived from the strain 2679 (KJ489414). A JEV-specific immune serum (obtain after vaccination against JEV) and monoclonal DENV-specific antibodies17 were used to perform direct immunofluorescence assays.

Preparation of cDNA Fragments

The complete genome flanked respectively in 5' and 3' by the human cytomegalovirus promoter (pCMV) (SEQ ID No:1) and the hepatitis delta ribozyme followed by the simian virus 40 polyadenylation signal (HDR/SV40 pA) (SEQ ID No:2) was amplified by PCR in three overlapping DNA fragments of approximately 4.8 kb, 3.0 kb and 4.3 kb (4.8 kb, 2.9 kb and 5.2 kb for CHIKV, 4.8 kb, 4.1 kb and 3.4 kb for TBEV and 2.9 kb, 2.8 kb and 2.7 kb for CV-B3) (see Table 1 under).

For WNV, TBEV, JEV III and CHIKV, DNA fragments were obtained by PCR using infectious clones (for JEV III, a mutation was corrected using fusion PCR).

For JEV I (all DNA fragments), DENV-4 (first and third fragments) and YFV (first and third fragments), DNA fragments were synthesized de novo (Genscript) and amplified by PCR. Amplicons were produced using the Platinum PCR SuperMix High Fidelity kit (Life Technologies).

The mixture (final volume: 50 μL) consisted of 45 μL of supermix, 2 μL of DNA template at 1 ng/μL (infectious clone or synthesized DNA fragment) and 200 nM of each primer. For DENV-4 and YFV, the second DNA fragment was obtained by RT-PCR from clarified cell supernatants. Nucleic acids were extracted using the EZ1 Virus Mini Kit v2 on the EZ1 Biorobot (both from Qiagen) according to the manufacturer's instructions and amplified with the Superscript III One-Step RT-PCR Platinum Taq Hifi kit (Life Technologies). The mixture (final volume: 50 μL) contained 25 μL of Reaction Mix, 2 μL of nucleic acid extract, 100 nM of each primer, 1 μL of Enzyme Mix and 20 μL of Nuclease-Free Water. Assays were performed on a Biometra T-professional Standard Gradient thermocycler with the following conditions: 94° C. for 2 min followed by 40 cycles of 94° C. for 15 sec, 64° C. for 30 sec, 68° C. for 5 min and a preliminary step of 50° C. for 30 min for the RT-PCR. Size of the PCR products was verified by gel electrophoresis and purified using Amicon Ultra—0.5 mL kit (Millipore) according to the manufacturer's instructions. When plasmid DNA was used as template, the complete removal of the template was ensured by a digestion step with the restriction enzyme Dpn1 (New England Biolabs) before transfection. To control the efficiency of this additional step, the inventors transfected (see below), as a control, only two cDNA fragments (the first and the second, 1 μg final). These controls did not produce any infectious virus.

TABLE 1

Primers used to obtain cDAN fragments

| Virus | cDNA Fragment | Primer Forward | Position | SEQ ID | Primer Reverse | Position | SEQ ID |
|---|---|---|---|---|---|---|---|
| JEV I | I | CACCCAACTGATCTTCAGCATCT | — | 3 | GAAGAATGATTCTGTAAGTGTCCAG | 4054-4078 | 4 |
| | II | CGTTGCCATGCCAATCTTAGCG | 4002-4023 | 5 | GGTGCTTGCGTCCTTCCACCAA | 6983-7004 | 6 |
| | III | CAAATGAGTATGGAATGCTGGAAAA | 6932-6956 | 7 | CTCAGGGTCAATGCCAGCGCTT | — | 8 |
| JEV II | I | GCCCACCGGAAGGAGCTGAC | — | 9 | CAGAGAGCAAATCCCTATGACGA | 4078-4100 | 10 |
| | II | CGTCACCATGCCAGTCTTAGCG | 4001-4022 | 11 | GCTTGGCAATCCAGTCAGTCCT | 7004-7025 | 12 |
| | III | CAAACGAGTACGGAATGCTAGAAA | 6931-6954 | 13 | CTCATGTTTGACAGCTTATCATCG | — | 14 |
| WNV | I | TCAATATTGGCCATTAGCCATATTAT | | 15 | TGGATTGAACACTCCTGTAGACGC | 4135-4158 | 16 |
| | II | TGGTTGGAGTTGGAAGCCTCATC | 4052-4074 | 17 | GACCATGCCGTGGCCGGCC | 7016-7034 | 18 |
| | III | TGGACAAGACCAAGAATGACATTG | 6920-6943 | 19 | GTTACAAATAAAGCAATAGCATCACA | — | 20 |
| TBEV | I | CAGGGTTATTGTCTCATGAGCGGA | — | 21 | GCCACGCCCAGGAAGAGCATGA | 4033-4054 | 22 |
| | II | GGGCCCTCTGGAAATGGGGAGA | 3892-3913 | 23 | CAACCCAGGCTTGTCACCATCTTT | 8003-8026 | 24 |
| | III | GGGTGAGGTCGTGGACCTTGGA | 7886-7907 | 25 | CCTAGGAATTTCACAAATAAAGCATTTT | — | 26 |

TABLE 1-continued

Primers used to obtain cDAN fragments

| Virus | cDNA Fragment | Primer Forward | Position | SEQ ID | Primer Reverse | Position | SEQ ID |
|---|---|---|---|---|---|---|---|
| YFV | I | CACCCAACTGATCTTCAGCATCT | — | 27 | GCATGGAAGTGTCCTTTGAGTTCT | 4071-4094 | 28 |
| | II | GACTTGCAACGATGCTCTTTTGCA | 4020-4043 | 29 | GAGAGAGCATCGTCACAATGCC | 7040-7061 | 30 |
| | III | GATTCCATCCAGCACCGCACC | 6964-6984 | 31 | CTCAGGGTCAATGCCAGCGCTT | — | 32 |
| DENV-4 | I | GAATAAGGGCGACACGGAAATGT | | 33 | TGAAGACAGCTTGTCCTGCACAA | — | 34 |
| | II | GATCATGGCTTGGAGGACCATTAT | 3980-4003 | 35 | GCTACTGCATAGAGCGTCCATG | 6949-6970 | 36 |
| | III | TTTACCAGGTAAAAACAGAAACCAC | 6892-6916 | 37 | CTCAGGGTCAATGCCAGCGCTT | | 38 |
| JEV I 6 fragments | I | CACCCAACTGATCTTCAGCATCT | | 39 | CATGGAACCATTCCCTATGGACT | 1635-1657 | 40 |
| | II | ACTGGATTGTGAACCAAGGAGTG | 1560-1582 | 41 | GAAGAATGATTCTGTAAGTGTCCAG | 4054-4078 | 42 |
| | III | CGTTGCCATGCCAATCTTAGCG | 4002-4023 | 43 | AATATAACCCCGAGCGGCGATG | 5511-5532 | 44 |
| | IV | ATGTCACCAAACAGGGTGCCCAA | 5440-5462 | 45 | GGTGCTTGCGTCCTTCCACCAA | 6983-7004 | 46 |
| | V | CAAATGAGTATGGAATGCTGGAAAA | 6932-6956 | 47 | GCGCCGTGCTCCATTGATTCTG | 8950-8971 | 48 |
| | VI | GGCTGTGGGCACATTTGTCACG | 8843-8864 | 49 | CTCAGGGTCAATGCCAGCGCTT | — | 50 |
| CHIKV | I | CACCCAACTGATCTTCAGCATCT | | 51 | CTGCTCGGGTGACCTGTCCTA | 4050-4070 | 52 |
| | II | TGAGATGTTTTTCCTATTCAGCAACT | 3961-3986 | 53 | AACAATGTGTTGACGAACAGAGTTA | 6966-6990 | 54 |
| | III | CTCCCTGCTGGACTTGATAGAG | 6859-6880 | 55 | CTCAGGGTCAATGCCAGCGCTT | — | 56 |
| CV-B3 | I | CACCCAACTGATCTTCAGCATCT | | 57 | CCACACAACATGCGTACCAAGCA | 2184-2206 | 58 |
| | II | CAGGCGCTGGCGCTCCGACA | 2148-2167 | 59 | GTCTATGGTTATACTCTCTGAACA | 4970-4994 | 60 |
| | III | GACAGGAGGACACAAGTCAGAT | 4921-4943 | 61 | CTCAGGGTCAATGCCAGCGCTT | — | 62 |

Cell Transfection

1 μg final of either an equimolar mix of all cDNA fragments amplified by PCR or 1 μg of infectious clone of CV-B3 was incubated with 12 μl of Lipofectamine 2000 (Life Technologies) in 600 μl of Opti-MEM medium (Life Technologies). According to the manufacturer's instructions, the mixture was added to a 12.5 cm2 culture flask of sub-confluent cells containing 1 mL of medium without antibiotics. After 4 hours of incubation, the cell supernatant was removed, cells were washed twice (HBSS; Life Technologies) and 3 mL of fresh medium was added. The cell supernatant was harvested when gross cytopathic effect (CPE) was observed (3-9 days depending on the cell type and the virus growth speed) or 9 days posttransfection for non cytopathic viruses, clarified by centrifugation, aliquoted and stored at −80° C. Each virus was then passaged four times using the same cell type except for the DENV-4 and YFV for which VeroE6 and HEK-293 were respectively used. Passages were performed by inoculating 333 μL of clarified cell supernatantonto cells in a 12.5 cm2 culture flask containing 666 μL of medium: after 2 hours of incubation, cells were washed twice (HBSS) and 3 mL of fresh medium was added. The cell supernatant was harvested after 2-6 days, clarified by centrifugation, aliquoted and stored at −80° C. Clarified cell supernatants (viruses stocks) were used to perform quantification of viral RNA, TCID50 assay, direct immunofluorescence assay and whole-genome sequencing.

Real Time PCR and RT-PCR Assays

To assess the production of infectious viruses and ensure that positive detection was not the result of cDNA contamination, viral RNA was quantified and compared with the quantity of detected cDNA using the Access RT-PCR Core Reagent kit (Promega) with or without the reverse transcriptase. RNA was extracted using the EZ1 mini virus 2.0 kit and the EZ1 Biorobot (both from Qiagen) according to the manufacturer's instructions. The mixture (final volume: 25 μL) contained a standard quantity of AMV/Tfl 5× Reaction Buffer, 0.5 μM of each primer, 0.5 μL of dNTP Mix, 0.5 mM of MgSO4, 0.5 μL of AMV reverse transcriptase (only for RT-PCR), 0.5 μL of Tfl DNA polymerase, 15.5 μL of Nuclease-Free Water and 2 μL of extracted nucleic acids. Assays were performed using the CFX96 Touch' Real-Time PCR Detection System (Biorad) with the following conditions: 50° C. for 15 min, 95° C. for 2 min, followed by 45 cycles of 95° C. for 15 sec, 60° C. for 40 sec. Data collection occurred during the 60° C. step. The difference between Cycle Threshold values (ct) obtained by Real time PCR and Real time RT-PCR assays has been used to assess viral RNA production. In addition, the amount of viral RNA expressed as dose detection limit (arbitrary unit; AU) was calculated from standard curves (nucleic acids from cell supernatants of cultured viruses were used as standard; five nucleic acid extracts were pooled and 10 μl-aliquots were stored at −80° C.).

Tissue Culture Infectious Dose 50 (TCID50) Assay

For each determination, a 96-well plate culture containing 20,000 BHK-21 cells in 100 μL of medium per well (added just before the inoculation) was inoculated with 50 μL of serial 10-fold dilutions of clarified cell culture supernatants: each row included 6 wells of the same dilution and two negative controls. The plates were incubated for 7 days and read for absence or presence of CPE in each well. The determination of the TCID50/mL was performed using the method of Reed and Muench18.

Direct Immuno-Fluorescence Assay (dIFA)

Direct IFA were performed using 12.5 cm2 culture flasks of SW13 cells for JEV I and JEV III, and VeroE6 cells infected respectively 2 and 6 days before using clarified cell supernatant (see above: passage of viruses). The supernatant was removed and the cells washed twice (HBSS; Invitrogen), trypsinised, harvested and diluted (1/5) with fresh medium. After cytocentrifugation of 150 μL of this cell suspension (3 min, 900 rpm; Cytospin, Thermo Scientific), the slides were dried, plunged 20 min in cold acetone for fixation, dried, incubated 30 min at 37° C. with appropriately diluted JEV-specific immune serum (see above) or monoclonal DENV-specific antibodies, washed twice with PBS, washed once with distilled water, dried, incubated 30 min at 37° C. with the appropriately diluted FITC-conjugated secondary antibody and Evans blue counterstain, washed twice with PBS, washed once with distilled water, dried, mounted and read using a fluorescence microscope.

Sequence Analysis of the Full-Length Genome

Complete genome sequencing was performed using the Ion PGM Sequencer19 (Life Technologies) and analyses conducted with the CLC Genomics Workbench 6 software. Virus supernatants were first clarified and treated with the Benzonase nuclease HC >99% (Novagen) at 37° C. overnight. Following RNA extraction (no RNA carrier was used; see above) using the EZ1 mini virus 2.0 kit and the EZ1 Biorobot (both from Qiagen), random amplification of nucleic acids was performed as previously described20. Amplified DNA was analysed using the Ion PGM Sequencer according to the manufacturer's instructions. The read obtained were trimmed: first using quality score, then by removing the primers used during the random amplification and finally at the 5' and 3' extremities by removing systematically 6 nucleotides. Only reads with a length greater than 29 nucleotides are used and mapped to the original genome sequence used as a reference. Mutation frequencies (proportion of viral genomes with the mutation) for each position were calculated simply as the number of reads with a mutation compared to the reference divided by the total number of reads at that site.

Results

The inventors developed a simple and versatile reverse genetics that facilitates the recovery of infectious RNA viruses from genomic DNA material without requiring cloning, propagation of cDNA into bacteria or in vitro RNA transcription. Their working hypothesis was that transfection of overlapping double-stranded DNA fragments, covering the entire genome of an RNA virus, into permissive cells would spontaneously enable recombination and synthesis of a DNA copy of the complete viral genome. By including at the 5' terminus of the first (5') DNA fragment, a promoter of DNA-dependent RNA polymerases, and at the 3' terminus of the last (3') DNA fragment a ribozyme sequence and a signal sequence for RNA poly-adenylation, the inventors anticipated that this genomic DNA copy would be transcribed as a full-length RNA genome with authentic 5' and 3' termini that would be efficiently exported out of the nucleus (in the case of a virus replicating in the cytoplasmic compartment).

The inventors first tested this hypothesis with 6 flaviviruses (i.e., arthropod-borne enveloped viruses with a single-stranded RNA genome of positive polarity that replicate in the cytoplasm of infected cells) that represent major flaviviral evolutionary lineages: two Japanese encephalitis viruses (JEV; genotype I (JEV I) and genotype III (JEV III)), one genotype 2 West Nile virus (WNV), one serotype 4 dengue virus (DENV-4), one wild-type strain of Yellow fever virus (YFV) and one Far-Eastern subtype Tick-borne encephalitis virus (TBEV) (Table 1).

Entire genomes were amplified by PCR in 3 DNA fragments of approximately 4 kb, each with 70-100 bp overlapping regions. The first and last fragments were flanked respectively in 5' and 3' by the human cytomegalovirus promoter (pCMV) and the hepatitis delta ribozyme followed by the simian virus 40 polyadenylation signal (HDR/SV40 pA) (FIG. 1). PCR products were column-purified, and 1 μg of an equimolar mix of all fragments was transfected into SW13 and/or BHK-21 cell lines, which, ensure efficient recovery of flaviviral infectious genomes. Cell supernatant media from these infectious cultures were serially passaged four times using the same cell types, enabling the isolation of JEV I, JEV III, TBEV and WNV. For more demanding viruses, isolation could be achieved by passaging in additional permissive cells (e.g., DENV-4: VeroE6 cells; YFV: HEK-293 cells). Virus replication after four serial passages was demonstrated for each virus using a combination of the following criteria:

(i) production of viral genomes in cell supernatant medium using real time RT-PCR methods, (ii) production of infectious particles in cell supernatant medium using TCID50 assays, (iii) detection of cytopathic effect (CPE), (iv) detection of viral antigens by direct immunofluorescence assays, and (v) complete viral genome sequencing using next generation sequencing (NGS) method.

The robustness, flexibility and versatility of the methods were further challenged as follows. Firstly, the inventors decreased the size and increased the number of overlapping fragments combined for transfection. This was exemplified in the case of JEV I, for which the ISA method generated infectious viruses, when using up to 6 overlapping amplicons of approximately 2 kb. Secondly, they applied the ISA method to viruses with a single-stranded RNA genome of positive polarity that belong to different families: Chikungunya virus (CHIKV, an enveloped virus, family Togaviridae) and Coxsackievirus B3 (CV-B3, a nonenveloped virus, family Picornaviridae). Again, infectious viruses could be isolated following transfection and four passages in HEK-293 cells (CHIKV) or BGM cells (CV-B3) (Table 2 under). Furthermore, the inventors used as a control the CV-B3 obtained following transfection of a plasmid-bearing infectious genome and they obtained similar results in terms of infectivity and sequence data (Table 2).

TABLE 2

Characterization of the recovered viruses

| Virus | Srain | Origin of the material used to produce subgenomic amplicons I | II | III | Cell line used for transfection | Cell line used during passages | Real time RT-PCR (U.A) | Log10 TCID50/ml | CPE |
|---|---|---|---|---|---|---|---|---|---|
| JEV | JEV I | DNS | DNS | DNS | BHK-21 | BHK-21 | 1.32E+08 | 5.8 | Yes |
| | | | | | SW13 | SW13 | 1.52E+07 | 5.2 | Yes |
| | | | | | SW13* | SW13* | 9.33E+06 | 2.8* | Yes |
| | JEV III | I.C. | I.C. | I.C. | BHK-21 | BHK-21 | 3.77E+07 | 6.1 | Yes |
| | | | | | SW13 | SW13 | 4.04E+06 | 4.8 | Yes |
| | Chimeric JEV I/JEV III | DNS | I.C. | I.C. | BHK-21 | BHK-21 | 9.33E+07 | 6.7 | Yes |
| | | | | | SW13 | SW13 | 1.00E+07 | 6.8 | Yes |
| | Chimeric JEV | I.C. | DNS | DNS | BHK-21 | BHK-21 | 6.58E+07 | 6.6 | Yes |

TABLE 2-continued

Characterization of the recovered viruses

| | | | | | | | | | |
|---|---|---|---|---|---|---|---|---|---|
| | III/JEV I | | | | SW13 | SW13 | 3.06E+07 | 6.4 | Yes |
| WNV | Ouganda | I.C. | I.C. | I.C. | BHK-21 | BHK-21 | 5.73E+07 | 5.3 | Yes |
| TBEV | Oshima 5.10 | I.C. | I.C. | I.C. | BHK-21 | BHK-21 | 3.28E+08 | 9.1 | Yes |
| DENV-4 | Dak HD 34 460 | DNS | Viral RNA | DNS | SW13 | VeroE6 | 6.59E+04 | N/A | No |
| YFV | BOL 88/1999 | DNS | Viral RNA | DNS | SW13 | HEK | 1.42E+05 | 5.2 | Yes |
| CHIKV | OPYI | I.C. | I.C. | I.C. | HEK-293 | HEK-293 | 2.01E+07 | 7 | Yes |
| CV-B3 | 2679 | I.C. | I.C. | I.C. | SW13 | BGM | 4.64E+07 | 7.4 | Yes |
| CV-B3¶ | 2679¶ | Not obtained by PCR¶ | | | SW13¶ | BGM¶ | 9.33E+07 | 7.4¶ | Yes |

| Virus | Srain | dIFA | dN/dS (all mutations) | dN/dS (fixed mutations) | Substitutions per site after 4 passages (all mutations) | Substitutions per site after 4 passages (fixed mutations) |
|---|---|---|---|---|---|---|
| JEV | JEV I | N/A | 3.273 | N/A | 1.27E+03 | 7.29E−04 |
| | | Positive | 0.409 | N/A | 7.29E+04 | 9.11E−05 |
| | | N/A | N/A | N/A | N/A | N/A |
| | JEV III | N/A | 1.286 | 1.143 | 1.54E−03 | 1.45E−03 |
| | | Positive | 0.536 | N/A | 6.37E−04 | — |
| | Chimeric JEV | N/A | 0.404 | 1.571 | 1.36E−03 | 3.64E−04 |
| | I/JEV III | N/A | 1.19 | 1.589 | 9.10E−04 | 7.28E−04 |
| | Chimeric JEV | N/A | 0.268 | 0.268 | 2.73E−04 | 2.73E−04 |
| | III/JEV I | N/A | 5.357 | 3.178 | 1.00E−03 | 6.38E−04 |
| WNV | Ouganda | N/A | 0.268 | N/A | 4.55E−04 | 2.73E−04 |
| TBEV | Oshima 5.10 | N/A | 3.214 | N/A | 7.20E−04 | 9.00E−05 |
| DENV-4 | Dak HD 34 460 | Positive | 0.436 | 0.535 | 8.45E−04 | 5.63E−04 |
| YFV | BOL 88/1999 | N/A | 0.818 | 0.818 | 4.63E−04 | 4.63E−04 |
| CHIKV | OPYI | N/A | 2.24 | N/A | 4.21E−04 | — |
| CV-B3 | 2679 | N/A | N/A | N/A | 2.70E−04 | — |
| CV-B3¶ | 2679¶ | N/A | N/A | N/A | — | — |

Summary of the different viruses produced in this study: the specific name of the strain, the origin of the initial material (DNS, De Novo Synthesis; I.C., Infectious Clone; or Viral RNA) used as the template for production of the first (I), second (II) and third (III) fragment, the cell line used for the transfection and the passages, the relative quantification of the amount of viral RNA and infectious titres in cell supernatants at the fourth passage by real time RT-PCR and TCID50 assay, the presence or absence of cytopathic effect (CPE) as well as the research of viral antigens by direct immunofluorescence assay (dIFA). Complete viral genome sequences were obtained using NGS technology. dN and dS correspond respectively to the number of non-synonymous substitutions per non-synonymous site and the number of synonymous substitutions per synonymous site. * Results obtained by transfection of six overlapping fragments. ¶ Results obtained by transfecting directly the CV-B3 plasmid-bearing infectious clone. N/A and AU mean not available and arbitrary unit respectively.

Thirdly, the inventors demonstrated the capability of ISA method to generate genetically modified viruses in days. This was exemplified by the PCR-based correction of a frame-shift mutation (1915del) in fragment one of a defective JEV III infectious clone and the subsequent recovery of the corresponding virus (Supplementary Methods). They were also able to produce chimeric viruses by exchanging the first DNA fragment (encoding structural proteins) of genotype I and III JEVs. Despite 11 mismatches in the overlapping region of the first two fragments, transfection resulted in the production of intergenotypic JEV I/JEV III and JEV III/JEV I chimeras. Analysis of complete genomic sequences established at the fourth passage, using NGS, showed that the genetic drift (rate of sequence change) was modest (ranging from 1.45E-03 to 9.00E-05 substitutions per site when considering fixed mutations). A majority of non-synonymous mutations, the presence of shared mutations amongst the different JEV strains (7/85), and the non-random distribution of mutations (at frequency above 10%) along the genome (with both hot spots and highly conserved regions) denoted adaptation to the cell culture conditions.

The mutation rate varied according to the cells used for isolation and, as expected, was higher in viruses derived from low-passage strains than in those derived from culture-adapted strains. In conclusion, the ISA method is a very simple procedure with which to expedite production of infectious genetically modified RNA viruses within days, with perfect control of the viral sequences and starting from a variety of initial sources including pre-existing infectious clones, viral RNA or de novo synthesized DNA genomic sequences. This technique has the future potential to generate the design of large reverse genetics experiments for RNA viruses, on a scale that could not previously have been considered. It also has the capacity, specifically to modulate the characteristics of the viruses recovered from experimental procedures. Additionally, because DNA subgenomic fragments can conveniently be obtained by PCR, this method has the potential to conserve the genetic diversity of viral populations13 when starting from viral RNA. Error-prone PCR may be also be used to create artificial viral heterogeneity, e.g. for facilitating the selection of adapted viruses15 under various experimental selection conditions and, conversely, high-fidelity polymerases and clonal amplification templates may be used to control the degree of clonality of the viruses produced.

Finally, the method of the invention has the potential to revolutionise the safety and security of future exchanges of RNA viruses between scientific institutions, by the separate shipment at room temperature of simple, on-infectious, DNA subgenomic fragments that, could then be combined and transfected by the recipient institute, enabling rapid, simple and safe recovery of the infectious viral strain.

Example 2

Method ISA with cDNA Fragments in Individual and Separate Plasmids

The inventors further illustrated the ISA method in the specific embodiment where step c) is a step of transfection of plasmids or vectors comprising a cDNA fragment obtained in step b), wherein each cDNA fragment is in individual and separate plasmid or vector.

This experiment was performed using three plasmids containing the same fragments of the Japanese Encephalitis virus genome (Genotype I, Laos strain) as those previously used for recovering infectious virus by the ISA method after PCR amplification.

The three plasmids were linearised by digestion with the restriction enzyme Fse I and directly transfected in equimolar quantity (1 μg final) into SW13 cells without prior PCR amplification. After 9 days and 1 passage, the virus was successfully recovered from culture.

Example 3

Application of the Method ISA In Vivo

Overlapping fragments covering the entire genome of RNA viruses and flanked respectively at 5 and 3' by promoter of DNA-dependent RNA polymerase and terminator/RNA polyadenylation signal were prepared using the method of the invention.

These DNA fragments were directly inoculated to live animals and allowed to recover infectious virus from several animal samples. In addition, clinical surveillance of animals (appearance of symptom and significant weight loss) allowed to observed typical signs of infection.

a) Experiment 1: Tick-borne Encephalitis Virus (TBEV; Flavivirus)

The inventors used a wild-type strain of tick-borne encephalitis virus (strain Oshima 5.10 (GenBank accession number AB062063)). They applied the method of the invention to DNA overlapping fragments.

Five-weeks-old C57Bl/6J female mice were inoculated with three DNA overlapping fragments.

The clinical course of the viral infection was monitored by following (i) the clinical manifestations of the disease (shivering, humpback, dirty eyes, hemi- or tetra-paresia, hemiplegia or tetraplegia); and (ii) the weight of the mice exactly as described by Fabritus L et al., 2015, Attenuation of Tick-Borne Encephalitis Virus Using Large-Scale Random Codon Re-encoding. PLoS Pathog 11(3).

Brains and spleens were collected from sacrificed mice 14 days post-inoculation. Brains and spleens were grounded and centrifuged. The resulting supernatant was used to assess the presence of infectious virus.

The presence of infectious virus was assessed using molecular (real time RT-PCR) and classical cell culture methods (isolation of infectious viruses).

Using an initial amount of DNA ranging between 2 to 5 μg, and two different inoculation routes (intraperitoneal and intradermal injections), infectious viruses were detected from both brains and spleens. Clinical manifestations (significant weight losses and symptoms) of the diseases were also observed.

b) Experiment 2: Intracerebral Inoculation of Suckling Mice

The inventors used wild-type strains of tick-borne encephalitis virus (strain Oshima 5.10 (GenBank accession number AB062063)) and Japanese encephalitis (JEV_CNS769_Laos_2009 (GenBank accession number KC196115)). They used the method of the invention to generate the DNA overlapping fragments.

DNA overlapping fragments were used diluted in PBS or were mixed with a transfection reagent.

Suckling OF1 mice were inoculated by intracerebral injection of DNA overlapping fragments. The clinical course of the viral infection was monitored by following the clinical manifestation of the disease (shivering, lethargy). Brains were collected from sacrificed mice 6-12 days post-inoculation. Brains were grounded and centrifuged. The resulting supernatant was used to assess the presence of infectious virus.

The presence of infectious virus was assessed using molecular (real time RT-PCR) and classical cell culture methods (isolation of infectious viruses).

Using 2 μg of DNA, infectious viruses were detected in brains for both viruses (TBEV and JEV) and with or without addition of transfection reagent. Clinical manifestations of the diseases were also observed.

The invention claimed is:

1. A method for generating an infectious RNA virus comprising:

a) introducing a promoter of DNA-dependent RNA polymerase in position 5' and optionally a terminator and a RNA polyadenylation sequence in position 3' of the entire genome of a RNA virus;

b) amplifying the entire viral genome as prepared in step a) including said promoter and optionally said terminator and RNA polyadenylation sequence, in at least 2, 3, 4, 5 or 6 overlapping cDNA fragments;

c) transfecting said cDNA fragments into a host cell, d) incubating the host cell of step c); and e) recovering the infectious RNA virus from said incubated host cell.

2. The method of claim 1, wherein said virus is a single stranded positive RNA virus.

3. The method of claim 1, wherein:

said promoter of DNA-dependent RNA polymerase in position 5' is the human cytomegalovirus promoter (pCMV) ; and/or said optional terminator and RNA polyadenylation sequence is respectively the hepatitis delta ribozyme and the simian virus 40 polyadenylation signal (HDR/SV40pA).

4. The method of claim 1, wherein step b) allows the production from 2 to 15 overlapping cDNA fragments.

5. The method of claim 1, wherein said host cell is selected from the group consisting of SW13 and BHK-21, HEK 293 and Vero cell lines.

6. The method of claim 5, wherein:

step (c) is a step of direct transfection of the cDNA fragments obtained in step (b) as such, and said step (c) occurs directly after step (b).

7. The method of claim 1, wherein step c) is a step of transfecting plasmids or vectors comprising a cDNA fragment obtained in step (b), wherein each cDNA fragment is included in an individual and separate plasmid or vector.

8. The method of claim 1, wherein said method further comprises a step (b') after step (b) and prior to step (c) of purification of the overlapping cDNA fragments.

9. The method of claim 1, wherein step (d) of incubation lasts from 3 to 9 days.

10. The method of claim 1, wherein the transfected cDNA fragments of step (c) spontaneously recombine in the host cells during the incubation step (d).

11. The method of claim 1 wherein said method is used for reverse genetic analysis.

12. The method of claim 2, wherein said virus is a virus selected from the group consisting of flavivirus, alphavirus and enterovirus.

13. The method according to claim 12, wherein said Flavivirus is selected from the group consisting of Japanese encephalitis viruses (JEV), West Nile virus (WNV); Dengue virus (DENV); Yellow fever virus (YFV); and Tick-borne encephalitis virus (TBEV).

14. The method according to claim 12, wherein said alphavirus is Chikungunya.

15. The method of claim 12, wherein said enterovirus is Coxsackie.

16. The method of claim 4, wherein step b) allows the production of 3, 4, 5 or 6 overlapping cDNA fragments.

17. The method of claim 8, wherein the purification step is through a chromatography column.

* * * * *

SEQUENCE LISTING

```
<160> NUMBER OF SEQ ID NOS: 62

<210> SEQ ID NO 1
<211> LENGTH: 781
<212> TYPE: DNA
<213> ORGANISM: Artificial Sequence
<220> FEATURE:
<223> OTHER INFORMATION: Promotor

<400> SEQUENCE: 1

gaataagggc gacacggaaa tgtcacccaa ctgatcttca gcatcttcaa tattggccat      60

tagccatatt attcattggt tatatagcat aaatcaatat tggctattgg ccattgcata     120
```

-continued

```
cgttgtatct atatcataat atgtacattt atattggctc atgtccaata tgaccgccat    180

gttggcattg attattgact agttattaat agtaatcaat tacggggtca ttagttcata    240

gcccatatat ggagttccgc gttacataac ttacggtaaa tggcccgcct ggctgaccgc    300

ccaacgaccc ccgcccattg acgtcaataa tgacgtatgt tcccatagta acgccaatag    360

ggactttcca ttgacgtcaa tgggtggagt atttacggta aactgcccac ttggcagtac    420

atcaagtgta tcatatgcca agtccgcccc ctattgacgt caatgacggt aaatggcccg    480

cctggcatta tgcccagtac atgaccttac gggactttcc tacttggcag tacatctacg    540

tattagtcat cgctattacc atggtgatgc ggttttggca gtacaccaat gggcgtggat    600

agcggtttga ctcacgggga tttccaagtc tccaccccat tgacgtcaat gggagtttgt    660

tttggcacca aaatcaacgg gactttccaa aatgtcgtaa taaccccgcc ccgttgacgc    720

aaatgggcgg taggcgtgta cggtgggagg tctatataag cagagctcgt ttagtgaacc    780

g                                                                    781


<210> SEQ ID NO 2
<211> LENGTH: 192
<212> TYPE: DNA
<213> ORGANISM: Artificial Sequence
<220> FEATURE:
<223> OTHER INFORMATION: HDR - SV40pA

<400> SEQUENCE: 2

ggccggcatg gtcccagcct cctcgctggc gccggctggg caacattccg aggggaccgt     60

cccctcggta atggcgaatg ggactcgcga cagacatgat aagatacatt gatgagtttg    120

gacaaaccac aactagaatg cagtgaaaaa aatgctttat ttgtgaaatt aagcgctggc    180

attgaccctg ag                                                        192


<210> SEQ ID NO 3
<211> LENGTH: 23
<212> TYPE: PRT
<213> ORGANISM: Artificial Sequence
<220> FEATURE:
<223> OTHER INFORMATION: primer F

<400> SEQUENCE: 3

Cys Ala Cys Cys Cys Ala Ala Cys Thr Gly Ala Thr Cys Thr Thr Cys
1               5                   10                  15

Ala Gly Cys Ala Thr Cys Thr
            20


<210> SEQ ID NO 4
<211> LENGTH: 25
<212> TYPE: DNA
<213> ORGANISM: Artificial Sequence
<220> FEATURE:
<223> OTHER INFORMATION: primer R

<400> SEQUENCE: 4

gaagaatgat tctgtaagtg tccag                                           25


<210> SEQ ID NO 5
<211> LENGTH: 22
<212> TYPE: DNA
<213> ORGANISM: Artificial Sequence
<220> FEATURE:
<223> OTHER INFORMATION: primer F

<400> SEQUENCE: 5
```

cgttgccatg ccaatcttag cg 22

<210> SEQ ID NO 6
<211> LENGTH: 22
<212> TYPE: DNA
<213> ORGANISM: Artificial Sequence
<220> FEATURE:
<223> OTHER INFORMATION: primer R

<400> SEQUENCE: 6
ggtgcttgcg tccttccacc aa 22

<210> SEQ ID NO 7
<211> LENGTH: 25
<212> TYPE: DNA
<213> ORGANISM: Artificial Sequence
<220> FEATURE:
<223> OTHER INFORMATION: primer F

<400> SEQUENCE: 7
caaatgagta tggaatgctg gaaaa 25

<210> SEQ ID NO 8
<211> LENGTH: 22
<212> TYPE: DNA
<213> ORGANISM: Artificial Sequence
<220> FEATURE:
<223> OTHER INFORMATION: primer R

<400> SEQUENCE: 8
ctcagggtca atgccagcgc tt 22

<210> SEQ ID NO 9
<211> LENGTH: 20
<212> TYPE: DNA
<213> ORGANISM: Artificial Sequence
<220> FEATURE:
<223> OTHER INFORMATION: primer F

<400> SEQUENCE: 9
gcccaccgga aggagctgac 20

<210> SEQ ID NO 10
<211> LENGTH: 23
<212> TYPE: DNA
<213> ORGANISM: Artificial Sequence
<220> FEATURE:
<223> OTHER INFORMATION: primer R

<400> SEQUENCE: 10
cagagagcaa atccctatga cga 23

<210> SEQ ID NO 11
<211> LENGTH: 22
<212> TYPE: DNA
<213> ORGANISM: Artificial Sequence
<220> FEATURE:
<223> OTHER INFORMATION: primer F

<400> SEQUENCE: 11
cgtcaccatg ccagtcttag cg 22

<210> SEQ ID NO 12
<211> LENGTH: 22
<212> TYPE: DNA

-continued

<213> ORGANISM: Artificial Sequence
<220> FEATURE:
<223> OTHER INFORMATION: primer R

<400> SEQUENCE: 12
gcttggcaat ccagtcagtc ct 22

<210> SEQ ID NO 13
<211> LENGTH: 24
<212> TYPE: DNA
<213> ORGANISM: Artificial Sequence
<220> FEATURE:
<223> OTHER INFORMATION: primer F

<400> SEQUENCE: 13
caaacgagta cggaatgcta gaaa 24

<210> SEQ ID NO 14
<211> LENGTH: 24
<212> TYPE: DNA
<213> ORGANISM: Artificial Sequence
<220> FEATURE:
<223> OTHER INFORMATION: primer R

<400> SEQUENCE: 14
ctcatgtttg acagcttatc atcg 24

<210> SEQ ID NO 15
<211> LENGTH: 26
<212> TYPE: DNA
<213> ORGANISM: Artificial Sequence
<220> FEATURE:
<223> OTHER INFORMATION: primer F

<400> SEQUENCE: 15
tcaatattgg ccattagcca tattat 26

<210> SEQ ID NO 16
<211> LENGTH: 24
<212> TYPE: DNA
<213> ORGANISM: Artificial Sequence
<220> FEATURE:
<223> OTHER INFORMATION: Primer R

<400> SEQUENCE: 16
tggattgaac actcctgtag acgc 24

<210> SEQ ID NO 17
<211> LENGTH: 23
<212> TYPE: DNA
<213> ORGANISM: Artificial Sequence
<220> FEATURE:
<223> OTHER INFORMATION: primer F

<400> SEQUENCE: 17
tggttggagt tggaagcctc atc 23

<210> SEQ ID NO 18
<211> LENGTH: 19
<212> TYPE: DNA
<213> ORGANISM: Artificial Sequence
<220> FEATURE:
<223> OTHER INFORMATION: primer R

<400> SEQUENCE: 18
gaccatgccg tggccggcc 19

<210> SEQ ID NO 19
<211> LENGTH: 24
<212> TYPE: DNA
<213> ORGANISM: Artificial Sequence
<220> FEATURE:
<223> OTHER INFORMATION: primer F

<400> SEQUENCE: 19
tggacaagac caagaatgac attg 24

<210> SEQ ID NO 20
<211> LENGTH: 26
<212> TYPE: DNA
<213> ORGANISM: Artificial Sequence
<220> FEATURE:
<223> OTHER INFORMATION: primer

<400> SEQUENCE: 20
gttacaaata aagcaatagc atcaca 26

<210> SEQ ID NO 21
<211> LENGTH: 24
<212> TYPE: DNA
<213> ORGANISM: Artificial Sequence
<220> FEATURE:
<223> OTHER INFORMATION: primer

<400> SEQUENCE: 21
cagggttatt gtctcatgag cgga 24

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
gccacgccca ggaagagcat ga 22

<210> SEQ ID NO 23
<211> LENGTH: 22
<212> TYPE: DNA
<213> ORGANISM: Artificial Sequence
<220> FEATURE:
<223> OTHER INFORMATION: primer

<400> SEQUENCE: 23
gggccctctg gaaatgggga ga 22

<210> SEQ ID NO 24
<211> LENGTH: 24
<212> TYPE: DNA
<213> ORGANISM: Artificial Sequence
<220> FEATURE:
<223> OTHER INFORMATION: primer

<400> SEQUENCE: 24
caacccaggc ttgtcaccat cttt 24

<210> SEQ ID NO 25
<211> LENGTH: 22
<212> TYPE: DNA
<213> ORGANISM: Artificial Sequence
<220> FEATURE:

-continued

<223> OTHER INFORMATION: primer

<400> SEQUENCE: 25
gggtgaggtc gtggaccttg ga 22

<210> SEQ ID NO 26
<211> LENGTH: 28
<212> TYPE: DNA
<213> ORGANISM: Artificial Sequence
<220> FEATURE:
<223> OTHER INFORMATION: primer

<400> SEQUENCE: 26
cctaggaatt tcacaaataa agcatttt 28

<210> SEQ ID NO 27
<211> LENGTH: 23
<212> TYPE: DNA
<213> ORGANISM: Artificial Sequence
<220> FEATURE:
<223> OTHER INFORMATION: primer

<400> SEQUENCE: 27
cacccaactg atcttcagca tct 23

<210> SEQ ID NO 28
<211> LENGTH: 24
<212> TYPE: DNA
<213> ORGANISM: Artificial Sequence
<220> FEATURE:
<223> OTHER INFORMATION: primer

<400> SEQUENCE: 28
gcatggaagt gtcctttgag ttct 24

<210> SEQ ID NO 29
<211> LENGTH: 24
<212> TYPE: DNA
<213> ORGANISM: Artificial Sequence
<220> FEATURE:
<223> OTHER INFORMATION: primer

<400> SEQUENCE: 29
gacttgcaac gatgctcttt tgca 24

<210> SEQ ID NO 30
<211> LENGTH: 22
<212> TYPE: DNA
<213> ORGANISM: Artificial Sequence
<220> FEATURE:
<223> OTHER INFORMATION: primer

<400> SEQUENCE: 30
gagagagcat cgtcacaatg cc 22

<210> SEQ ID NO 31
<211> LENGTH: 21
<212> TYPE: DNA
<213> ORGANISM: Artificial Sequence
<220> FEATURE:
<223> OTHER INFORMATION: primer

<400> SEQUENCE: 31
gattccatcc agcaccgcac c 21

<210> SEQ ID NO 32
<211> LENGTH: 22
<212> TYPE: DNA
<213> ORGANISM: Artificial Sequence
<220> FEATURE:
<223> OTHER INFORMATION: primer

<400> SEQUENCE: 32
ctcagggtca atgccagcgc tt 22

<210> SEQ ID NO 33
<211> LENGTH: 23
<212> TYPE: DNA
<213> ORGANISM: Artificial Sequence
<220> FEATURE:
<223> OTHER INFORMATION: primer

<400> SEQUENCE: 33
gaataagggc gacacggaaa tgt 23

<210> SEQ ID NO 34
<211> LENGTH: 23
<212> TYPE: DNA
<213> ORGANISM: Artificial Sequence
<220> FEATURE:
<223> OTHER INFORMATION: primer

<400> SEQUENCE: 34
tgaagacagc ttgtcctgca caa 23

<210> SEQ ID NO 35
<211> LENGTH: 24
<212> TYPE: DNA
<213> ORGANISM: Artificial Sequence
<220> FEATURE:
<223> OTHER INFORMATION: primer

<400> SEQUENCE: 35
gatcatggct tggaggacca ttat 24

<210> SEQ ID NO 36
<211> LENGTH: 22
<212> TYPE: DNA
<213> ORGANISM: Artificial Sequence
<220> FEATURE:
<223> OTHER INFORMATION: primer

<400> SEQUENCE: 36
gctactgcat agagcgtcca tg 22

<210> SEQ ID NO 37
<211> LENGTH: 25
<212> TYPE: DNA
<213> ORGANISM: Artificial Sequence
<220> FEATURE:
<223> OTHER INFORMATION: primer

<400> SEQUENCE: 37
tttaccaggt aaaaacagaa accac 25

<210> SEQ ID NO 38
<211> LENGTH: 22
<212> TYPE: DNA
<213> ORGANISM: Artificial Sequence
<220> FEATURE:
<223> OTHER INFORMATION: primer

<400> SEQUENCE: 38
ctcagggtca atgccagcgc tt 22

<210> SEQ ID NO 39
<211> LENGTH: 23
<212> TYPE: DNA
<213> ORGANISM: Artificial Sequence
<220> FEATURE:
<223> OTHER INFORMATION: primer

<400> SEQUENCE: 39
cacccaactg atcttcagca tct 23

<210> SEQ ID NO 40
<211> LENGTH: 23
<212> TYPE: DNA
<213> ORGANISM: Artificial Sequence
<220> FEATURE:
<223> OTHER INFORMATION: primer

<400> SEQUENCE: 40
catggaacca ttccctatgg act 23

<210> SEQ ID NO 41
<211> LENGTH: 23
<212> TYPE: DNA
<213> ORGANISM: Artificial Sequence
<220> FEATURE:
<223> OTHER INFORMATION: primer

<400> SEQUENCE: 41
actggattgt gaaccaagga gtg 23

<210> SEQ ID NO 42
<211> LENGTH: 25
<212> TYPE: DNA
<213> ORGANISM: Artificial Sequence
<220> FEATURE:
<223> OTHER INFORMATION: primer

<400> SEQUENCE: 42
gaagaatgat tctgtaagtg tccag 25

<210> SEQ ID NO 43
<211> LENGTH: 22
<212> TYPE: DNA
<213> ORGANISM: Artificial Sequence
<220> FEATURE:
<223> OTHER INFORMATION: primer

<400> SEQUENCE: 43
cgttgccatg ccaatcttag cg 22

<210> SEQ ID NO 44
<211> LENGTH: 22
<212> TYPE: DNA
<213> ORGANISM: Artificial Sequence
<220> FEATURE:
<223> OTHER INFORMATION: primer

<400> SEQUENCE: 44
aatataaccc cgagcggcga tg 22

<210> SEQ ID NO 45
<211> LENGTH: 23

-continued

<212> TYPE: DNA
<213> ORGANISM: Artificial Sequence
<220> FEATURE:
<223> OTHER INFORMATION: primer

<400> SEQUENCE: 45
atgtcaccaa acagggtgcc caa 23

<210> SEQ ID NO 46
<211> LENGTH: 22
<212> TYPE: DNA
<213> ORGANISM: Artificial Sequence
<220> FEATURE:
<223> OTHER INFORMATION: primer

<400> SEQUENCE: 46
ggtgcttgcg tccttccacc aa 22

<210> SEQ ID NO 47
<211> LENGTH: 25
<212> TYPE: DNA
<213> ORGANISM: Artificial Sequence
<220> FEATURE:
<223> OTHER INFORMATION: primer

<400> SEQUENCE: 47
caaatgagta tggaatgctg gaaaa 25

<210> SEQ ID NO 48
<211> LENGTH: 22
<212> TYPE: DNA
<213> ORGANISM: Artificial Sequence
<220> FEATURE:
<223> OTHER INFORMATION: primer

<400> SEQUENCE: 48
gcgccgtgct ccattgattc tg 22

<210> SEQ ID NO 49
<211> LENGTH: 22
<212> TYPE: DNA
<213> ORGANISM: Artificial Sequence
<220> FEATURE:
<223> OTHER INFORMATION: primer

<400> SEQUENCE: 49
ggctgtgggc acatttgtca cg 22

<210> SEQ ID NO 50
<211> LENGTH: 22
<212> TYPE: DNA
<213> ORGANISM: Artificial Sequence
<220> FEATURE:
<223> OTHER INFORMATION: primer

<400> SEQUENCE: 50
ctcagggtca atgccagcgc tt 22

<210> SEQ ID NO 51
<211> LENGTH: 23
<212> TYPE: DNA
<213> ORGANISM: Artificial Sequence
<220> FEATURE:
<223> OTHER INFORMATION: primer

<400> SEQUENCE: 51
cacccaactg atcttcagca tct 23

<210> SEQ ID NO 52
<211> LENGTH: 21
<212> TYPE: DNA
<213> ORGANISM: Artificial Sequence
<220> FEATURE:
<223> OTHER INFORMATION: primer

<400> SEQUENCE: 52
ctgctcgggt gacctgtcct a 21

<210> SEQ ID NO 53
<211> LENGTH: 26
<212> TYPE: DNA
<213> ORGANISM: Artificial Sequence
<220> FEATURE:
<223> OTHER INFORMATION: primer

<400> SEQUENCE: 53
tgagatgttt ttcctattca gcaact 26

<210> SEQ ID NO 54
<211> LENGTH: 25
<212> TYPE: DNA
<213> ORGANISM: Artificial Sequence
<220> FEATURE:
<223> OTHER INFORMATION: primer

<400> SEQUENCE: 54
aacaatgtgt tgacgaacag agtta 25

<210> SEQ ID NO 55
<211> LENGTH: 22
<212> TYPE: DNA
<213> ORGANISM: Artificial Sequence
<220> FEATURE:
<223> OTHER INFORMATION: primer

<400> SEQUENCE: 55
ctccctgctg gacttgatag ag 22

<210> SEQ ID NO 56
<211> LENGTH: 22
<212> TYPE: DNA
<213> ORGANISM: Artificial Sequence
<220> FEATURE:
<223> OTHER INFORMATION: primer

<400> SEQUENCE: 56
ctcagggtca atgccagcgc tt 22

<210> SEQ ID NO 57
<211> LENGTH: 23
<212> TYPE: DNA
<213> ORGANISM: Artificial Sequence
<220> FEATURE:
<223> OTHER INFORMATION: primer

<400> SEQUENCE: 57
cacccaactg atcttcagca tct 23

<210> SEQ ID NO 58
<211> LENGTH: 23
<212> TYPE: DNA
<213> ORGANISM: Artificial Sequence -continued

```
<220> FEATURE:
<223> OTHER INFORMATION: primer

<400> SEQUENCE: 58

ccacacaaca tgcgtaccaa gca                                              23


<210> SEQ ID NO 59
<211> LENGTH: 20
<212> TYPE: DNA
<213> ORGANISM: Artificial Sequence
<220> FEATURE:
<223> OTHER INFORMATION: primer

<400> SEQUENCE: 59

caggcgctgg cgctccgaca                                                  20


<210> SEQ ID NO 60
<211> LENGTH: 24
<212> TYPE: DNA
<213> ORGANISM: Artificial Sequence
<220> FEATURE:
<223> OTHER INFORMATION: primer

<400> SEQUENCE: 60

gtctatggtt atactctctg aaca                                             24


<210> SEQ ID NO 61
<211> LENGTH: 22
<212> TYPE: DNA
<213> ORGANISM: Artificial Sequence
<220> FEATURE:
<223> OTHER INFORMATION: primer

<400> SEQUENCE: 61

gacaggagga cacaagtcag at                                               22


<210> SEQ ID NO 62
<211> LENGTH: 22
<212> TYPE: DNA
<213> ORGANISM: Artificial Sequence
<220> FEATURE:
<223> OTHER INFORMATION: primer

<400> SEQUENCE: 62

ctcagggtca atgccagcgc tt                                               22
```